(12) United States Patent
Futatsuka et al.

(10) Patent No.: US 9,709,473 B2
(45) Date of Patent: Jul. 18, 2017

(54) METHOD AND APPARATUS FOR MEASURING DYNAMIC PANEL STIFFNESS OF OUTER PANEL FOR AUTOMOBILE PARTS

(71) Applicant: JFE Steel Corportion, Tokyo (JP)

(72) Inventors: Takayuki Futatsuka, Tokyo (JP); Takashi Iwama, Tokyo (JP); Kentaro Sato, Tokyo (JP); Yuji Yamasaki, Tokyo (JP); Youiti Komatu, Tokyo (JP); Eiichi Shiraishi, Tokyo (JP); Kazunari Yoshitomi, Tokyo (JP); Yukiko Hata, Tokyo (JP); Kayo Tokieda, Tokyo (JP)

(73) Assignee: JFS Steel Corporation (JP)

( * ) Notice: Subject to any disclaimer, the term of this patent is extended or adjusted under 35 U.S.C. 154(b) by 225 days.

(21) Appl. No.: 14/437,861

(22) PCT Filed: Oct. 30, 2013

(86) PCT No.: PCT/JP2013/079386
§ 371 (c)(1),
(2) Date: Apr. 23, 2015

(87) PCT Pub. No.: WO2014/069518
PCT Pub. Date: May 8, 2014

(65) Prior Publication Data
US 2015/0292999 A1    Oct. 15, 2015

(30) Foreign Application Priority Data

Nov. 5, 2012   (JP) ................ 2012-243614

(51) Int. Cl.
G01N 3/42      (2006.01)
G01M 11/08   (2006.01)
G01N 3/06      (2006.01)

(52) U.S. Cl.
CPC ............ G01N 3/42 (2013.01); G01M 11/081 (2013.01); G01N 3/068 (2013.01); G01N 2203/0647 (2013.01)

(58) Field of Classification Search
CPC .................... G01N 3/42; G01N 3/46
See application file for complete search history.

(56) References Cited

U.S. PATENT DOCUMENTS 4,304,133 A * 12/1981 Feamster, III ......... B23Q 1/621
                                                                        73/633
4,331,026 A *  5/1982 Howard .................. G01N 3/42
                                                                        340/680

(Continued)

FOREIGN PATENT DOCUMENTS

CN   202433272      9/2012
JP   58-86436 A     5/1983

(Continued)

OTHER PUBLICATIONS

Chinese Office Action dated Jun. 3, 2016, of corresponding Chinese Application No. 201380055723.5, along with an English translation of the Search Report.

(Continued)

*Primary Examiner* — Paul West
*Assistant Examiner* — Mark A Shabman
(74) *Attorney, Agent, or Firm* — DLA Piper LLP (US)

(57) ABSTRACT

A method of measuring panel stiffness of an automobile part outer panel by pushing an indenter onto a surface of the panel in a pushing direction intersecting the surface under a load to deform the panel and measuring deformation of the panel includes arranging grids in a lattice form to a surface of a site of the panel; arranging markers previously knowing three-dimensional position information on a periphery of the site; pushing the indenter onto the surface of the site under the load and moving the indenter in a direction perpendicu- (Continued)

lar to the pushing direction, during which the grids on the surface deformed by loading of the indenter are simultaneously and repeatedly shot from plural positions by plural cameras; and calculating position information of the grids corresponding to the markers based on the image data to measure change in deformation of the panel associated with movement of the indenter.

10 Claims, 4 Drawing Sheets

(56) References Cited

U.S. PATENT DOCUMENTS

| | | | | | |
|---|---|---|---|---|---|
| 4,463,600 | A | * | 8/1984 | Hobbs | G01B 11/285 356/626 |
| 4,463,607 | A | | 8/1984 | Hilton | |
| 4,621,523 | A | * | 11/1986 | Shabel | G01N 3/42 73/81 |
| 4,945,490 | A | * | 7/1990 | Biddle, Jr. | G01N 3/42 356/626 |
| 4,969,106 | A | * | 11/1990 | Vogel | G01B 11/165 382/108 |
| 5,699,444 | A | * | 12/1997 | Palm | G01C 11/06 348/42 |
| 7,649,628 | B2 | * | 1/2010 | Wadman | G01N 21/4738 356/445 |
| 7,716,989 | B2 | * | 5/2010 | Kollgaard | G01N 27/90 73/627 |
| 2008/0148863 | A1 | * | 6/2008 | Thompson | G01M 5/005 73/788 |
| 2013/0047712 | A1 | * | 2/2013 | Ariga | G01N 3/42 73/81 |
| 2013/0119106 | A1 | * | 5/2013 | Moyal | B28D 1/225 225/2 |

FOREIGN PATENT DOCUMENTS

| | | |
|---|---|---|
| JP | 59-009542 A | 1/1984 |
| JP | 61-045953 A | 3/1986 |
| JP | 62-070730 A | 4/1987 |
| JP | 01-197627 A | 8/1989 |
| JP | 04-134243 A | 5/1992 |
| JP | 6-18947 U | 3/1994 |
| JP | 07-14857 B | 4/1995 |
| JP | 3072735 U | 8/2000 |
| JP | 2009-115775 A | 5/2009 |
| JP | 2009-204468 A | 9/2009 |

OTHER PUBLICATIONS

Supplementary European Search Report dated Oct. 12, 2015 of corresponding European Application No. 13851774.3.
Notice of Ground for Rejection dated Sep. 2, 2015 of corresponding Japanese Application No. 2014-544549 along with an English translation.

* cited by examiner

METHOD AND APPARATUS FOR MEASURING DYNAMIC PANEL STIFFNESS OF OUTER PANEL FOR AUTOMOBILE PARTS

TECHNICAL FIELD

This disclosure relates to a method and apparatus for measuring dynamic panel stiffness of an outer panel for automobile parts.

BACKGROUND

As one of performances of an outer panel required for automobile parts such as doors, engine hoods, roofs or the like is dynamic panel stiffness. If the dynamic panel stiffness is lacking, so-called buckling sound by snap through is generated during car washing by applying a moving load to the outer panel with a palm, a cloth or the like along a form of the panel or during the wiping operation in waxing, whereby the quality feeling of the automobile is damaged significantly. Particularly in recent years, the buckling sound tends to be easily generated due to panel thinning associated with weight-saving of automobile body and diversification of panel design. Hence, securing dynamic panel stiffness becomes a significant issue with car manufacturers.

Heretofore, evaluation of dynamic panel stiffness of the outer panel is carried out as follows. That is, JP-A-S59-009542 discloses a method wherein the outer panel is deformed by pushing an indenter onto a certain site of the outer panel, during which a relationship between load and displacement of indenter is converted into an electric signal that is recorded. In that method, the indenter can be separated from a measuring base to push the indenter onto the outer panel assembled into the automobile body and the load is measured by a load cell disposed on the indenter, and the displacement is calculated by integrating signal of an acceleration meter disposed on the indenter twice.

JP-A-S62-070730 discloses a method wherein an indenter of a panel stiffness measuring head integrally united with a load meter and a displacement meter is pushed onto a certain site of an outer panel transversely mounted onto the measuring base to deform the outer panel and a load is measured by the load meter. In that method, the indenter is pushed at the predetermined load to deform the outer panel to accurately perform the measurement of panel stiffness. The displacement meter is reset to zero at the deformed state and then the displacement quantity of the indenter is measured until completion of unloading while decreasing the load by retracting the indenter from the deformed state.

JU-A-H06-018947 discloses a method wherein panel stiffness of the outer panel in the automobile body is measured by attaching a pressing test unit to a robot arm. To accurately measure the snap through of the outer panel by that method, an indenter made from a subcolumnar aluminum material is attached to the pressing test unit through a load cell for the load measurement. The pressing test unit is moved to a front of a certain site of the outer panel and thereafter the indenter is pushed onto the outer panel with a hydraulic cylinder driven by a hydraulic hand pump to measure displacement of the indenter with a dial gauge.

JU-B-H07-014857 discloses a method of measuring panel stiffness of a roof panel for automobile body. In that method, a support member is supported by an arm horizontally extending above the automobile body to prevent a decrease in measuring accuracy due to misalignment between load meter and pressing shaft in the measuring operation, and the pressing shaft that applies a load to the roof panel is elevatably supported and a displacement meter for detecting a moving quantity of the pressing shaft is supported by the support member. Further, a slider provided with a load meter opposing to a rear end portion of the pressing shaft is elevatably supported and an air cylinder elevating the slider is supported by the support member, and the slider is allowed to fall by the air cylinder to move the pressing shaft downwardly through the load meter and the certain site of the roof panel is deformed by the pressing shaft to measure displacement of the pressing shaft with the displacement meter.

However, those conventional methods of measuring static panel stiffness evaluate load displacement of only the certain site of the outer panel pushed by the indenter so that it is impossible to evaluate the behavior of sequentially changing a deformation zone of the outer panel by moving the indenter to apply a moving load based on reproduction of a wiping operation of moving a palm, a cloth or the like along the surface of the panel while applying a constant load.

As to dynamic panel stiffness of the outer panel, a simple sensory evaluation has been hitherto performed in the manufacturing floor. In that evaluation, an inspector judges the presence or absence of generating the buckling sound by stroking the outer panel along its curved face with a palm, a cloth or the like while applying a load to determine an acceptance of the panel. Although the judgment of acceptance on the presence or absence of generating the buckling sound by such a simple sensory evaluation is sufficient in the manufacturing floor or quality assurance site, a quantitative evaluation way is required to study improvement of dynamic panel stiffness in the development stage. In the quantitative evaluation, acoustic data of the buckling sound can be analyzed to collect information such as loudness (sound pressure level), tone (frequency) and the like in addition to the presence or absence of generating the buckling sound, and it is possible to evaluate dynamic panel stiffness in detail. Also, to identify a decisive influence on dynamic panel stiffness, it is important to grasp deformation behavior of the outer panel. Further, to verify accuracy of simulation in performance prediction, it is necessary to compare the deformation state of the panel between analysis and measured result. To this end, it is desired to develop a technology of measuring dynamic panel stiffness in a higher accuracy.

It could, therefore, be helpful to provide a method and an apparatus for measuring dynamic panel stiffness of an outer panel for automobile parts.

SUMMARY

We thus provide a method of measuring dynamic panel stiffness of an outer panel for automobile parts by pushing an indenter onto a surface of an outer panel to be measured in a given pushing direction intersecting to the surface under a given load to deform the outer panel and measuring a deformation state of the outer panel, characterized in that grids arranged in a regular lattice form are transferred to a surface of a measuring site of the outer panel to be measured;

fiducial markers previously knowing three-dimensional position information are arranged on the periphery of the measuring site of the outer panel;

the indenter is pushed onto the surface of the measuring site of the outer panel under the load and moved in a direction perpendicular to the pushing direction, during which the grids on the surface of the outer panel deformed by loading of the indenter are simultaneously and repeatedly shot from plural positions by plural cameras;

three-dimensional position information of the grids is calculated corresponding to the fiducial markers based on the shot image data to measure a change in the deformation state of the outer panel associated with the movement of the indenter, which is output as panel deformation data.

In the method of measuring dynamic panel stiffness of an outer panel for automobile parts, it is preferable that the pushing direction is a downward direction and the load for pushing the indenter to the surface of the outer panel is set on the basis of a weight disposed on the indenter.

The downward direction as the pushing direction is not limited to a vertical downward direction and may be inclined within ±20° with respect to the vertical downward direction.

In the method of measuring dynamic panel stiffness of an outer panel, it is also preferable that sound generated in the deformation of the outer panel by loading of the indenter is collected by a sound collecting means and output as acoustic data.

Further, we provide an apparatus for measuring dynamic panel stiffness of an outer panel for automobile parts by pushing an indenter onto a surface of an outer panel to be measured in a given pushing direction intersecting to the surface under a given load to deform the outer panel and measuring a deformation state of the outer panel, characterized by comprising grids arranged in a regular lattice form and transferred to a surface of a measuring site of the outer panel to be measured;

fiducial markers previously knowing three-dimensional position information and arranged on the periphery of the measuring site of the outer panel;

an indenter pushing and moving means for pushing the indenter onto a surface of a measuring site of the outer panel to be measured under the above load and moving the indenter in a direction perpendicular to the pushing direction;

a plurality of cameras simultaneously and repeatedly shooting the grids on the surface of the outer panel deformed by loading of the indenter from plural positions; and a calculation means of calculating three-dimensional position information of the grids corresponding to the fiducial markers based on image data shot by the plural cameras and measuring a change in deformation state of the outer panel associated with the movement of the indenter to output as panel deformation data.

In the apparatus for measuring dynamic panel stiffness of an outer panel for automobile parts, it is preferable that the pushing direction is a downward direction and the load for pushing the indenter to the surface of the outer panel is set on the basis of a weight disposed on the indenter.

The downward direction as the pushing direction is not limited to a vertical downward direction and may be inclined within ±20° with respect to the vertical downward direction.

Also, the apparatus for measuring dynamic panel stiffness of an outer panel preferably comprises a sound collecting means collecting sound generated in the deformation of the outer panel by loading of the indenter and outputting as acoustic data.

Further, the apparatus for measuring dynamic panel stiffness of an outer panel preferably comprises a dynamic panel stiffness evaluating means that evaluates dynamic panel stiffness of the outer panel based on the panel deformation data and the acoustic data.

According to the method of measuring dynamic panel stiffness of the outer panel for automobile parts, the grids arranged in a regular lattice form are transferred to the surface of the measuring site of the outer panel to be measured, and the fiducial markers previously knowing three-dimensional position information are arranged on the periphery of the measuring site of the outer panel, and the indenter is pushed onto the surface of the measuring site of the outer panel under the load and moved in a direction perpendicular to the pushing direction, during which the grids on the surface of the outer panel deformed by loading of the indenter are shot simultaneously and repeatedly with the plural cameras from plural positions, and three-dimensional position information of the grids is calculated corresponding to the fiducial markers based on the shot image data to measure a change in the deformation state of the outer panel associated with the movement of the indenter, which is output as panel deformation data so that load in generating the buckling sound due to the snap through and the deformation behavior of the outer panel resulting from the moving load can be measured quantitatively, whereby a series of panel deformation behavior associated with the movement of the indenter can be evaluated quantitatively in automobile parts such as doors, hoods, roofs and the like, and a way of improving the dynamic panel stiffness of the outer panel for automobile parts can be attained in a rational manner.

Further, according to the method of measuring dynamic panel stiffness of the outer panel for automobile parts by collecting sound generated in the deformation of the outer panel by loading of the indenter with a sound collecting means and outputting it as acoustic data, the grids arranged in a regular lattice form are transferred to the surface of the measuring site of the outer panel to be measured, and the fiducial markers previously knowing three-dimensional position information are arranged on the periphery of the measuring site of the outer panel, and the indenter is pushed onto the surface of the measuring site of the outer panel under the load and moved in a direction perpendicular to the pushing direction, during which the grids on the surface of the outer panel deformed by loading of the indenter are shot simultaneously and repeatedly with the plural cameras from plural positions, and three-dimensional position information of the grids is calculated corresponding to the fiducial markers based on the shot image data to measure a change in the deformation state of the outer panel associated with the movement of the indenter, which is output as panel deformation data, while sound generated in the deformation of the outer panel associated with the movement of the indenter is collected with the sound collecting means and output as acoustic data so that it is possible to evaluate dynamic panel stiffness of the outer panel in detail from sound pressure level, frequency zone and the like of the buckling sound generated when the moving load is applied to the outer panel in the automobile parts such as doors, engine hoods, roofs and the like, and also the identification of load in generating the buckling sound and a series of panel deformation behavior associated with the movement of the indenter can be evaluated quantitatively, whereby it is made possible to identify factors of parts shape and structure exerting, for example, the sound pressure level, and a way of improving the dynamic panel stiffness of the outer panel for automobile parts can be attained in a rational manner.

On the other hand, according to the apparatus for measuring dynamic panel stiffness of the outer panel for automobile parts, the grids arranged in a regular lattice form are transferred to the surface of the measuring site of the outer panel, and the fiducial markers previously knowing three-dimensional position information are arranged on the periphery of the measuring site of the outer panel, and the indenter pushing and moving means pushes the indenter onto the surface of the measuring site of the outer panel under the load and moves the indenter in a direction perpendicular to the pushing direction, and the plural cameras shoot simultaneously and repeatedly the grids on the surface of the outer panel deformed by loading of the indenter from the plural positions, and the calculation means calculates three-dimensional information of the grids corresponding to the fiducial markers based on the image data shot by the plural cameras to measure a change in the deformation state of the outer panel associated with the movement of the indenter and output as panel deformation data so that load in generating the buckling sound due to the snap through and the deformation behavior of the outer panel resulting from the moving load can be measured quantitatively by performing our method, whereby a series of panel deformation behavior associated with the movement of the indenter can be evaluated quantitatively in automobile parts such as doors, hoods, roofs and the like, and a way of improving the dynamic panel stiffness of the outer panel for automobile parts can be attained in a rational manner.

Further, according to the apparatus for measuring dynamic panel stiffness of the outer panel for automobile parts provided with the dynamic panel stiffness evaluating means that evaluates dynamic panel stiffness of the outer panel based on the panel deformation data and the acoustic data, the grids arranged in a regular lattice form are transferred to the surface of the measuring site of the outer panel, and the fiducial markers previously knowing three-dimensional position information are arranged on the periphery of the measuring site of the outer panel, and the indenter pushing and moving means pushes the indenter onto the surface of the measuring site of the outer panel under the load and moves the indenter in a direction perpendicular to the pushing direction, and the plural cameras shoot simultaneously and repeatedly the grids on the surface of the outer panel deformed by loading of the indenter from the plural positions, and the calculation means calculates three-dimensional information of the grids corresponding to the fiducial markers based on the image data shot by the plural cameras to measure a change in the deformation state of the outer panel associated with the movement of the indenter and output as panel deformation data, and further the sound collecting means collects sound generated in the deformation of the outer panel by loading of the indenter and outputs as acoustic data so that it is possible to evaluate dynamic panel stiffness of the outer panel in detail from sound pressure level, frequency zone and the like of the buckling sound generated when the moving load is applied to the outer panel in the automobile parts such as doors, engine hoods, roofs and the like, and also the identification of load in generating the buckling sound and a series of panel deformation behavior associated with the movement of the indenter can be evaluated quantitatively, whereby it is made possible to identify factors of parts shape and structure exerting, for example, the sound pressure level, and a way of improving the dynamic panel stiffness of the outer panel for automobile parts can be attained in a rational manner.

Figure 1:
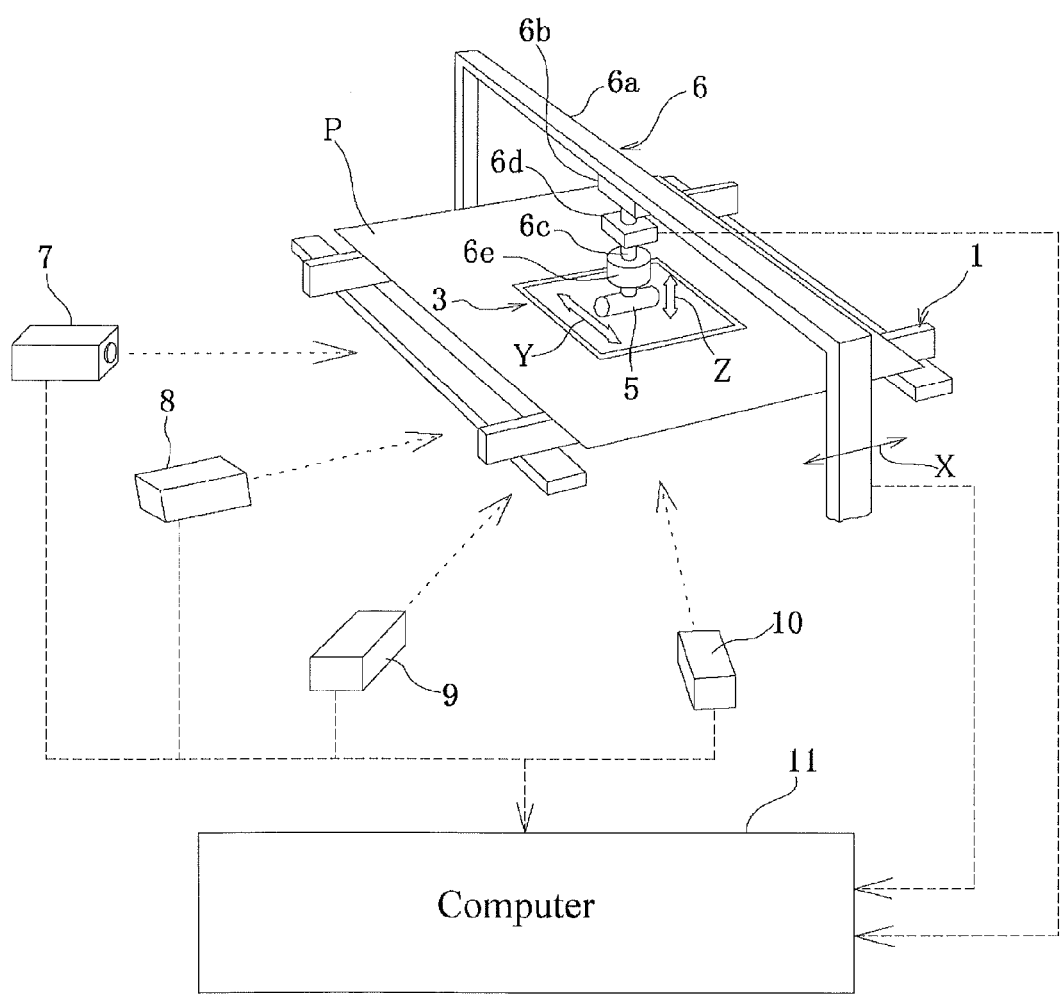
FIG. 1 is a schematic view illustrating an example of the apparatus for measuring dynamic panel stiffness of an outer panel for automobile parts which is used in an example of the method of measuring dynamic panel stiffness of an outer panel for automobile parts.

DESCRIPTION OF REFERENCE SYMBOLS 1 panel support base
2 grid
3 outer frame
4 fiducial marker
5 indenter
6 horizontally indenter moving device
7, 8, 9, 10 digital camera
11 computer
12 microphone
P panel to be measured

DETAILED DESCRIPTION

An example of our apparatus will be described in detail with reference to the accompanying drawings below. FIG. 1 is a schematic view illustrating an example of the apparatus for measuring dynamic panel stiffness of an outer panel for automobile parts which is used in an example of the method of measuring dynamic panel stiffness of an outer panel for automobile parts, and FIG. 2 is a plane view illustrating an example of a grid pattern used in the example of the apparatus for measuring dynamic panel stiffness of an outer panel for automobile parts, and FIG. 3 is a perspective view illustrating an example of a fiducial marker used in the example of the apparatus for measuring dynamic panel stiffness of an outer panel for automobile parts.

Figure 2:
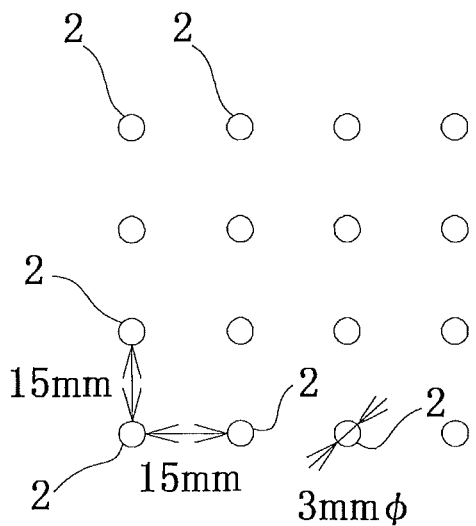
FIG. 2 is a plane view illustrating an example of a grid pattern used in the example of the apparatus for measuring dynamic panel stiffness of an outer panel for automobile parts.
Figure 3:
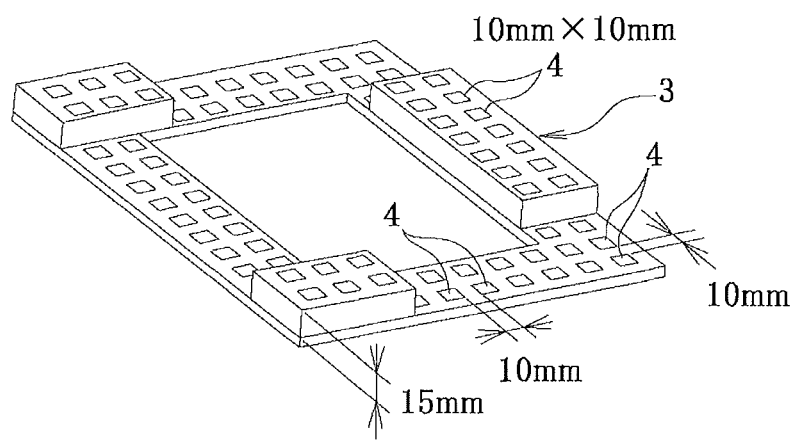
FIG. 3 is a perspective view illustrating an example of a fiducial marker used in the example of the apparatus for measuring dynamic panel stiffness of an outer panel for automobile parts.

The example of the apparatus for measuring dynamic panel stiffness of an outer panel for automobile parts measures a deformation state of an outer panel to be measured by pushing an indenter onto the surface of the outer panel in a given pushing direction intersecting to the surface under a given load to deform the outer panel, and comprises a support base 1 for an outer panel P to be measured fixing and supporting the panel at a substantially horizontal state as shown in FIG. 1, grids 2 previously formed on a surface of a measuring site of the outer panel P supported by the support base 1 and arranged in a regular lattice form as shown in FIG. 2, an outer frame 3 arranged on the periphery of the measuring site of the outer panel P supported by the support base 1, fiducial markers 4 indicated on the outer frame 3 as shown in FIG. 3 and previously knowing three-dimensional position information, and an indenter 5 pushing onto the surface of the measuring site of the outer panel P supported by the support base 1 in a given pushing direction intersecting to the surface, or a vertical downward direction shown by an arrow Z.

Also, the example of the apparatus for measuring dynamic panel stiffness of an outer panel for automobile parts comprises a horizontally indenter moving device 6 as an indenter pushing and moving means for pushing the indenter 5 onto the surface of the outer panel P supported by the support base 1 under a given load and moving in a direction perpendicular to the pushing direction, or a horizontal direction shown by an arrow Y, a plurality of cameras simultaneously and repeatedly shooting the grids 2 on the surface of the outer panel P deformed by loading of the indenter 5, or four digital cameras 7~10 in this example, and a usual computer 11 as a calculator/calculation means of calculating three-dimensional position information of the grids 2 corresponding to the fiducial markers 4 based on image data shot by the digital cameras 7~10 to measure a change in the deformation state of the outer panel associated with the movement of the indenter 5 and outputting onto a viewing surface of a display device not shown.

The grids 2 illustrated in FIG. 2 are circles with a diameter of 3 mm and are arranged at intervals of 15 mm in two directions perpendicular to each other to form a regular lattice pattern. The grids 2 can be formed, for example, by transferring a grid pattern along the surface of the measuring site of the outer panel P through coating or etching, or by attaching a grid pattern printed on a soft or hard film to the surface of the measuring site of the outer panel P, or by directly marking or printing a grid pattern to the surface of the measuring site surface of the outer panel P.

The fiducial markers 4 illustrated in FIG. 3 are indicated on a frame part and a thick-plate part of an outer frame 3 formed, for example, by mounting a plurality of thick-plate parts of 15 min in thickness onto a rectangular frame part, and are squares of 10 mm in both length and are arranged at intervals of 10 mm in two directions perpendicular to each other to form a regular lattice pattern. Moreover, three-dimensional position information of these fiducial markers 4 is previously known.

The horizontally indenter moving device 6 illustrated in FIG. 1 comprises a portal arm 6a with a central portion thereof horizontally extending in a given y-axis direction, a x-axis driving mechanism (not shown) horizontally moving the portal arm 6a in a x-axis direction perpendicular to the extending direction of the central portion and shown by an arrow X, a head 6b movably supported to the central portion of the portal arm 6a therealong, a y-axis driving mechanism (not shown) horizontally moving the head 6b along the central portion of the portal arm 6a in a y-axis direction shown by an arrow Y, a displacement meter detecting a y-axis moving quantity, a pressing rod 6c supported at its top end by the head 6b to elevatably move in a z-axis direction being a vertical direction shown by an arrow Z and maintain a posture of its axial line extending in the z-axis direction, a displacement meter 6d detecting an elevating quantity of the pressing rod 6c, and a weight 6e disposed to a middle portion of the pressing rod 6c and applying a load to the indenter 5. To the lower end of the pressing rod 6c is disposed the indenter 5.

The indenter 5 can be freely moved in up and down directions by the elevation of the pressing rod 6c. Also, the indenter 5 moves on the surface of the panel P to be measured smoothly so that the surface thereof contacting with the panel P is preferable to have a curved form to always stabilize the contact between the panel P and the indenter 5 in accordance with the complicated form of the panel. Further, the length of the indenter 5 (width perpendicular to the moving direction) is not more than 200 mm assuming the wiping operation of the outer panel with the palm, and 100 mm in this example. The indenter 5 is pressed onto the panel P by pushing onto the panel P under a total load of deadweights of the weight 6e, pressing rod 6c and indenter 5 so that the load applied to the panel P is constant. The adjustment of the load can be performed, for example, by changing the weight 6e with one having a different deadweight.

When the method of measuring dynamic panel stiffness of an outer panel for automobile parts is performed by using the apparatus for measuring the dynamic panel stiffness of the outer panel for automobile parts according to the above example, the grids 2 are first transferred onto the surface of the measuring site of the panel P to be measured as an outer panel for automobile parts, and then the peripheral portion of the panel P is fixed and supported onto the panel support base 1, and thereafter the outer frame 3 indicating the fiducial markers 4 is placed on the periphery of the surface of the measuring site of the panel P. The fiducial markers 4 are shot by four digital cameras 7~10 fixed at predetermined positions, and then the fiducial markers 4 are removed from the panel P, and thereafter the indenter 5 is pushed onto the measuring site of the panel P from above under a load adjusted as mentioned above to flexibly deform the measuring site of the panel P down. Subsequently, the indenter 5 is horizontally moved in y-axis direction by the horizontally indenter moving device 6 to apply the moving load of the indenter 5 to the measuring site of the panel P, while the grids 2 on the surface of the measuring site of the panel P are shot simultaneously and repeatedly by the four digital cameras 7~10 until the movement of the indenter 5 by the given distance is completed. The horizontal and elevating moving distances of the indenter 5 during the shooting are input to the computer 11 to continuously record these distances in substance.

The shot images are also input to and recorded by the computer 11 and arithmetic processing of these images is performed as mentioned later to calculate three-dimensional position information of each of the grids 2, which is output and displayed on a viewing surface of a display device as panel deformation data. The changing state of the surface form of the panel P associated with the movement of the indenter 5 can be measured from these three-dimensional position information of the grids 2 in a higher accuracy so that it is possible to perform understanding of deformation behavior of the outer panel in generating the buckling sound, identification of load and hence measurement of dynamic panel stiffness of the outer panel in a high accuracy.

There will be described the position measuring theory through optical means when three-dimensional position information of the grids 2 is calculated by the computer 11 corresponding to the fiducial markers 4 based on the image data shot with the four digital cameras 7~10 (which are called as cameras 1~4 hereinafter) below. Moreover, the position measuring theory has previously disclosed in detail in JP-A-2009-204468 so that the outline thereof is described below.

When a point X in a three-dimensional space (X, Y, Z) is shot by a digital camera located at a certain position in space, two-dimensional pixel M (x, y) of the digital camera is projected as shown by Equation (1):

$$\lambda M = PX = A[RT]X \tag{1}$$

wherein $\lambda$ is an arbitrary real number. Also, A is a matrix converting a physical coordinate into an image coordinate and is called as a camera calibration matrix. Further, R and T are matrices defining a direction and position in camera space. Moreover, matrix P defined by A, R and T is called as a camera matrix.

A, R and T are constituted as shown by Equation (2):

$$A = \begin{bmatrix} a_u & s & u_0 \\ 0 & a_v & v_0 \\ 0 & 0 & 1 \end{bmatrix}, R = \begin{bmatrix} r_{11} & r_{12} & r_{13} \\ r_{21} & r_{22} & r_{23} \\ r_{31} & r_{32} & r_{33} \end{bmatrix}, T = \begin{bmatrix} T_X \\ T_Y \\ T_Z \end{bmatrix} \quad (2)$$

Five parameters ($a_u$, $a_v$, $u_0$, $v_0$, s) of the camera calibration matrix A are values inherent to the camera calculated from focal length of the camera, coordinate of image center, scale factors in x- and y-directions and shear coefficient. Since the position and direction of the camera are changed at every measurement, it is necessary to identify R and T matrices in each case. In the method, the after-mentioned method may be used for identifying 12 parameters in total constituting the R and T matrices.

Starting the process, the previously known internal parameter A of the digital camera is first set to acquire digital images of the cameras 1~4. Then, fiducial markers 4 in the digital image are recognized by image processing to acquire two-dimensional coordinate of each pattern. Moreover, three-dimensional coordinate of this pattern is assumed to be previously known. Since the acquired two-dimensional coordinate and three-dimensional coordinate of the fiducial marker 4 are related to the aforementioned equation (1), 12 parameters of unknown R and T can be calculated by inputting two-dimensional coordinate and three-dimensional coordinate corresponded to the equation (1). In this case, identification accuracy of R and T is improved as the number of recognized points becomes larger.

At this stage can be determined R and T matrices, from which the camera matrix P is calculated together with the internal parameter A as shown in Equation (3):

$$P = A[RT] = \begin{bmatrix} P_{11} & P_{12} & P_{13} & P_{14} \\ P_{21} & P_{22} & P_{23} & P_{24} \\ P_{31} & P_{32} & P_{33} & P_{34} \end{bmatrix}. \quad (3)$$

Next, grid pattern in the digital image is recognized from the digital images of the cameras 1~4 by image processing to acquire two-dimensional coordinate of the center of each grid 2 in the grid pattern. This processing is repeated for the position-different four cameras 1~4. Then, a process of restoring to three-dimensional shape is performed from the grid patterns recognized by the four cameras 1~4 with the camera matrix P known by the above processing. At first, two-dimensional coordinate of an arbitrary grid P1 [k] is acquired from the images of the cameras 1~4.

Next, Equation (4) is obtained by rewriting Equation (1) with the camera parameters P:

$$\lambda \begin{bmatrix} x \\ y \\ 1 \end{bmatrix} = \begin{bmatrix} P_{11} & P_{12} & P_{13} & P_{14} \\ P_{21} & P_{22} & P_{23} & P_{24} \\ P_{31} & P_{32} & P_{33} & P_{34} \end{bmatrix} \begin{bmatrix} X \\ Y \\ Z \\ 1 \end{bmatrix}. \quad (4)$$

Equation (5) is derived from camera parameters of each camera 1, 2, two-dimensional coordinates (x, y) and (x', y').

Since formulae of unknown X, Y and Z are 4 in this equation, three-dimensional coordinates of X, Y and Z can be deduced by using a generalized inverse matrix.

$$\begin{bmatrix} P_{31}x - P_{11} & P_{32}x - P_{12} & P_{33}x - P_{13} \\ P_{31}y - P_{21} & P_{32}y - P_{22} & P_{33}y - P_{23} \\ P'_{31}x' - P'_{11} & P'_{32}x' - P'_{12} & P'_{33}x' - P'_{13} \\ P'_{31}y' - P'_{21} & P'_{32}y' - P'_{22} & P'_{33}y' - P'_{23} \end{bmatrix} \begin{bmatrix} X \\ Y \\ Z \end{bmatrix} = \begin{bmatrix} P_{14} - P_{34}x \\ P_{24} - P_{34}y \\ P'_{14} - P'_{34}x' \\ P'_{24} - P'_{34}y' \end{bmatrix} \quad (5)$$

Three-dimensional coordinate X12 is deduced from P1 [k] and P2 [j] with the above equation. As to the validity of the resulting three-dimensional coordinate (X, Y, Z), it is verified whether or not it is included in the measuring zone. If it is an unrealistic coordinate, subsequent processing of P2 is conducted. When valid three-dimensional coordinate (X, Y, Z) is obtained by repeating this processing, accession of grid coordinate P3 [l] of the camera 3 is conducted successively. Three-dimensional coordinate is deduced from three points P1 [k], P2 [j] and P3 [l] by the similar processing. The validity of the calculated three-dimensional coordinate is verified again. Further, grid coordinate P4 [m] of the camera 4 is acquired to deduce three-dimensional coordinate from four points P1 [k], P2 [j], P3 [l] and P4 [m].

Then, the validity of the determined three-dimensional coordinate is verified. At a stage of determining three-dimensional coordinated deduced from two-dimensional coordinates of four points, a process of re-projecting the three-dimensional coordinate into two-dimensional coordinate every each of the four cameras is performed using the relation of the equation (1). An error of the re-projected two-dimensional coordinate to the original two-dimensional coordinate P1 [k], P2 [j], P3 [l], P4 [m] is examined. By repeating this processing is determined a combination of four two-dimensional coordinates to minimize an error after the re-projection. The three-dimensional coordinate minimizing the error is determined, a value of which is registered to a database.

This processing is repeated to all of P1 [k] to end the processing. By the above processing can be determined three-dimensional coordinates of the grids 2 transferred to the panel P from the images of the digital cameras 7~10.

According to the aforementioned method and apparatus for measuring dynamic panel stiffness of the outer panel for automobile parts, the load in generating the buckling sound due to the snap through resulted from the moving load and the wide-range deformation behavior of the outer panel can be measured and evaluated quantitatively.

Figure 4:
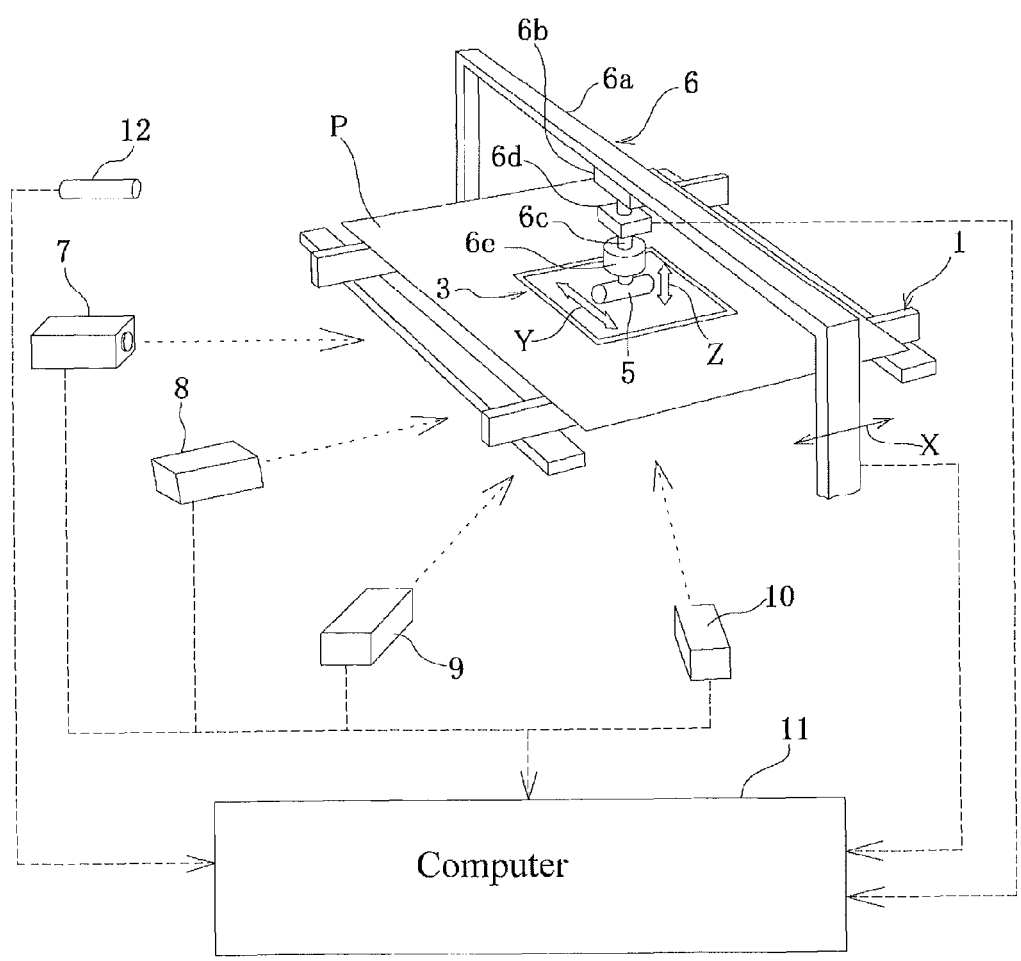
FIG. 4 is a schematic view illustrating another example of the apparatus for measuring dynamic panel stiffness of an outer panel for automobile parts which is used in another example of the method of measuring dynamic panel stiffness of an outer panel for automobile parts.

FIG. 4 is a schematic view of another example of the apparatus for measuring dynamic panel stiffness of the outer panel for automobile parts used in another example of the method of measuring dynamic panel stiffness of the outer panel for automobile parts. In this case, parts similar to the aforementioned example are represented by the same symbols.

That is, this example of the apparatus for measuring dynamic panel stiffness of the outer panel for automobile parts also measures the deformation state of the outer panel to be measured by pushing the indenter onto the surface of the outer panel in a given pushing direction intersecting to the surface under a given load to deform the outer panel. As shown in FIG. 4, it comprises a panel support base 1 fixing and supporting an outer panel P substantially at a horizontal state, grids 2 previously indicated on a surface of a measuring site of the outer panel P supported by the panel support base 1 and arranged in a regular lattice form as shown in FIG. 2, an outer frame 3 disposed on the periphery of the measuring site of the outer panel P supported by the panel support base 1, fiducial markers 4 with the previously known three-dimensional position information indicated on the outer frame 3 as shown in FIG. 3, and an indenter 5 pushed onto the surface of the measuring site of the outer panel P supported by the panel support base 1 in a given pushing direction intersecting to the surface or in a vertical direction shown by an arrow z downward. Moreover, the grids 2 and the fiducial markers 4 are the same as used in the aforementioned examples so that detailed explanation thereof is omitted here.

Further, this example of the apparatus for measuring dynamic panel stiffness of the outer panel for automobile parts comprises a horizontally indenter moving device 6 as an indenter pushing and moving means by pushing the indenter 5 onto the surface of the measuring site of the outer panel P supported by the panel support base 1 under a given load and moving in a direction perpendicular to the pushing direction or in a horizontal direction shown by an arrow Y in this example, plural cameras simultaneously and repeatedly shooting the grids 2 on the surface of the outer panel P deformed by the load of the indenter 5 from plural positions or four digital cameras 7~10 in this example, a usual computer 11 as a calculation means by calculating three-dimensional position information of the grids 2 corresponding to the fiducial markers 4 based on the image data shot by the digital cameras 7~10 to measure a change in the deformation state of the outer panel associated with the movement of the indenter 5 and outputting it on a viewing surface of a display device not shown as deformation data of the outer panel, and further a usual microphone 12 as a sound collector/collecting means by collecting sound generated in the deformation of the outer panel P by loading of the indenter 5, inputting into the computer 11 as acoustic data and outputting on the viewing surface of the display device. Moreover, the indenter 5 and the horizontally indenter moving device 6 are the same as used in the former example so that detailed explanation thereof is omitted here.

When the method of measuring dynamic panel stiffness of an outer panel for automobile parts according to this example is performed by using the apparatus for measuring the dynamic panel stiffness of the outer panel for automobile parts according to the above example, the grids 2 are first transferred onto the surface of the measuring site of the panel P to be measured as an outer panel for automobile parts, and then the peripheral portion of the panel P is fixed and supported onto the panel support base 1, and thereafter the outer frame 3 indicating the fiducial markers 4 is placed on the periphery of the surface of the measuring site of the panel P. The fiducial markers 4 are shot by four digital cameras 7~10 arranged on predetermined positions, and then the fiducial markers 4 are removed from the panel P, and thereafter the indenter 5 is pushed onto the measuring site of the panel P from above under a load adjusted as mentioned above to flexibly deform the measuring site of the panel P down. Subsequently, the indenter 5 is horizontally moved in y-axis direction by the horizontally indenter moving device 6 to apply the moving load of the indenter 5 to the measuring site of the panel P, while the grids 2 on the surface of the measuring site of the panel P are shot simultaneously and repeatedly by the four digital cameras 7~10 until the movement of the indenter 5 by the given distance is completed. The horizontal and elevating moving distances of the indenter 5 during the shooting are input to the computer 11 to continuously record these distances in substance. Further, the microphone 12 continuously collects sound generated from the panel P during movement of the indenter 5 with the horizontally indenter moving device 6 while applying the moving load of the indenter 5 to the measuring site of the panel P and converts into acoustic data as an electric signal and inputs to the computer 11. Also, the acoustic data are continuously recorded by the computer 11 in substance.

The shot images are also input to and recorded by the computer 11 and arithmetic processing of these images is performed as mentioned later to calculate three-dimensional position information of each of the grids 2, which is output and displayed on a viewing surface of a display device as panel deformation data. Moreover, the position measuring theory through optical means when three-dimensional position information of the grids 2 is calculated by the computer 11 corresponding to the fiducial markers 4 based on the image data shot with the four digital cameras 7~10 (which are called as cameras 1~4 hereinafter) is the same as described in the former example so that the detailed explanation thereof is omitted here. The changing state of the surface form of the panel P associated with the movement of the indenter 5 can be measured from these three-dimensional position information of the grids 2 in a higher accuracy so that it is possible to perform understanding of deformation behavior of the outer panel in generating the buckling sound, identification of load and hence measurement of dynamic panel stiffness of the outer panel in a high accuracy.

Figure 5:
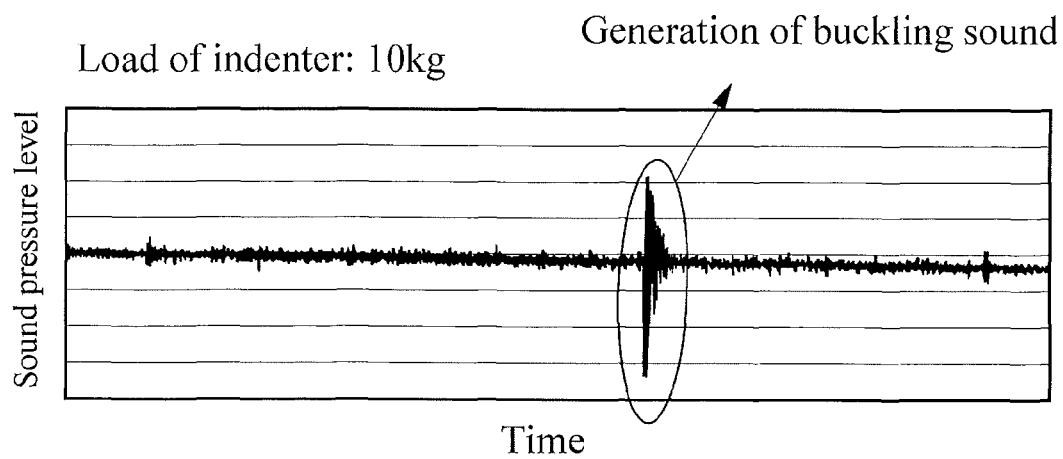
FIG. 5 is a graph showing an example of acoustic data from sounds collected in the deformation of the outer panel with the above example of the apparatus for measuring dynamic panel stiffness of an outer panel for automobile parts, wherein (a) shows acoustic data in generating buckling sound and (b) shows acoustic data in not generating buckling sound.
Figure 5:
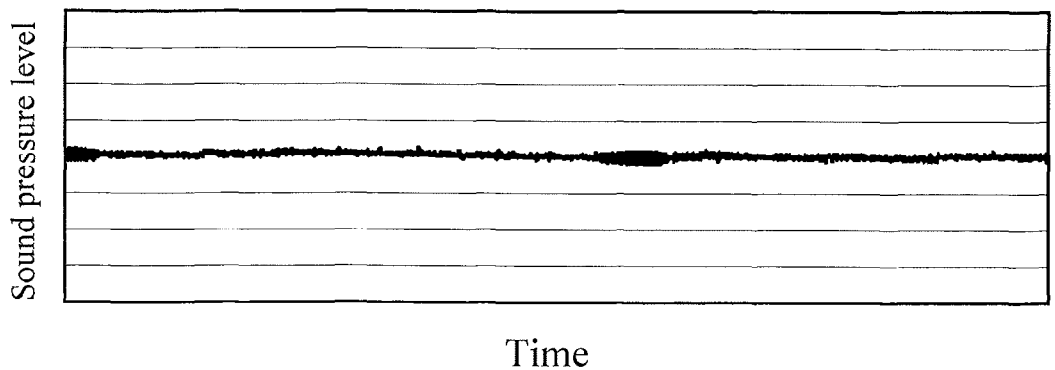

Also, the computer 11 outputs and displays the acoustic data of the sound generated from the panel P with the movement of the indenter 5 on the viewing surface of the display device. FIG. 5 is a graph of an example of the acoustic data of sounds collected in the deformation of the outer panel with the apparatus for measuring dynamic panel stiffness of the outer panel for automobile parts according to the above example as a change with time of a treble sound pressure level when audible frequency range for human is divided into a treble zone and a bass zone, wherein (a) shows acoustic data in generating buckling sound and (b) shows acoustic data in not generating buckling sound.

When the method of measuring dynamic panel stiffness of an outer panel for automobile parts according to this example is performed by using the apparatus for measuring the dynamic panel stiffness of the outer panel for automobile parts according to the above example, the computer 11 further evaluates dynamic panel stiffness of the panel P based on the panel deformation data and acoustic data as an evaluation means of dynamic panel stiffness and outputs the evaluation result on the viewing surface of the display device.

That is, the computer 11 divides the acoustic data into plural zones of audible frequency range for human, for example, a treble zone of not less than 400 Hz and a bass zone of less than 400 Hz by filtering and sets defect sound pressure threshold level to make it lower in the treble zone that the buckling sound is harsh on the ear and higher in the bass zone that the buckling sound is enough to be ignored as compared to the treble zone. When generation of the snap through of the panel P resulting from the moving load is judged from the change with time of the panel deformation data, the computer compares peaks in the change with time of sound pressure levels at these zones with the defect sound pressure threshold values in these zones, and performs the evaluation more fitting to human's feeling as compared to the evaluation of the buckling sound simply collected over the whole of the audible frequency range, and outputs the evaluated results.

According to the method and apparatus for measuring dynamic panel stiffness of the outer panel for automobile parts as mentioned above, it is possible to minutely evaluate dynamic panel stiffness of the outer panel in automobile parts such as doors, engine hoods, roofs and so on from sound pressure level, frequency range and the like of the buckling sound generated when the moving load is applied to the outer panel and to quantitatively evaluate the identification of load in generating the buckling sound and a series of deformation behavior of the panel associated with the movement of the indenter, whereby it is made possible to identify factors of parts shape and structure exerting, for example, the sound pressure level, and a way of improving the dynamic panel stiffness of the outer panel for automobile parts can be attained in a rational manner.

Although the above is described with reference to the drawings, this disclosure is not limited to the above example and may be modified properly within the scope of claims, if necessary. For example, the indenter 5 may be a cylindrical, round bar-shaped or semispherical member fixed to the lower end portion of the pushing rod 6c to render the curved surface into a downward direction. Also, an air cylinder applying, for example, a constant load to the indenter 5 may be used instead of the weight 6e. The number of the cameras may be 2 as long as the fixing position is known. As the number becomes larger, the measuring accuracy can be enhanced.

In the above examples, the grids 2 transferred to the surface of the panel P at a side pressed by the indenter 5 are shot by the digital cameras 7~10. However, the grids 2 may be transferred to a surface of the panel P at a rear side opposing to the side pressed by the indenter 5 and the fiducial markers 4 are supported to the surface of the rear side by magnets or the like, in which the fiducial markers 4 and grids 2 may be successively shot by the digital cameras 7~10 without being obstructed by the indenter 5.

In the above examples, load is applied with the indenter 5 in the vertical downward direction while supporting the panel P at substantially a horizontal state. However, the pushing direction of the indenter 5 is not limited to the vertical downward direction and may be inclined within ±20° with respect to the vertical downward direction. Also, load may be applied into a horizontal direction with the indenter 5 by giving a constant load with a crank arm suspending, for example, the air cylinder or weight while supporting the panel P in substantially a vertical direction as in an attaching posture to the vehicle body.

In the above examples, the microphone 12 is used as the sound collecting means, but a pick-up coil electromagnetically detecting vibrations of the panel P, a piezo element mechanically detecting vibrations of the panel P or the like may be used instead of the microphone.

INDUSTRIAL APPLICABILITY

According to the method and apparatus for measuring dynamic panel stiffness of the outer panel for automobile parts can be quantitatively measured and evaluated the load in generating the buckling sound due to the snap through and the wide-ranging deformation behavior of the outer panel.

The invention claimed is:

1. A method of measuring dynamic panel stiffness of an outer panel for automobile parts by pushing an indenter onto a surface of an outer panel to be measured in a selected pushing direction intersecting the surface under a selected load to deform the outer panel and measuring a deformation state of the outer panel comprising:

transferring grids arranged in a regular lattice form to a surface of a measuring site of the outer panel to be measured;

arranging fiducial markers indicating predetermined three-dimensional position information on a periphery of the measuring site of the outer panel;

pushing the indenter onto the surface of the measuring site of the outer panel under the load and moving the indenter in a direction perpendicular to the pushing direction, during which the grids on the surface of the outer panel deformed by loading of the indenter are simultaneously and repeatedly shot from plural positions by plural cameras; and calculating three-dimensional position information of the grids corresponding to the fiducial markers based on the shot image data to measure a change in the deformation state of the outer panel associated with the movement of the indenter, which is output as panel deformation data.

2. The method according to claim 1, wherein the pushing direction is a downward direction and the load that pushes the indenter to the surface of the outer panel is selected on the basis of a weight disposed on the indenter.

3. The method according to claim 2, wherein sound generated in deformation of the outer panel by loading of the indenter is collected by a sound collector and output as acoustic data.

4. The method according to claim 1, wherein sound generated in deformation of the outer panel by loading of the indenter is collected by a sound collector and output as acoustic data.

5. An apparatus for measuring dynamic panel stiffness of an outer panel for automobile parts by pushing an indenter onto a surface of an outer panel to be measured in a selected pushing direction intersecting to the surface under a selected load to deform the outer panel and measuring a deformation state of the outer panel, comprising:

grids arranged in a regular lattice form and transferred to a surface of a measuring site of the outer panel to be measured;

fiducial markers indicating predetermined three-dimensional position information and arranged on the periphery of the measuring site of the outer panel;

an indenter pusher and mover that pushes the indenter onto a surface of a measuring site of the outer panel under the above load and moves the indenter in a direction perpendicular to the pushing direction;

a plurality of cameras simultaneously and repeatedly shooting the grids on the surface of the outer panel deformed by loading of the indenter from plural positions; and a calculator calculating three-dimensional position information of the grids corresponding to the fiducial markers based on image data shot by the plural cameras and measuring a change in deformation state of the outer panel associated with the movement of the indenter to output as panel deformation data.

6. The apparatus according to claim 5, wherein the pushing direction is a downward direction and the load that pushes the indenter to the surface of the outer panel is selected on the basis of a weight disposed on the indenter.

7. The apparatus according to claim 6, wherein the apparatus comprises a sound collector collecting sound generated in deformation of the outer panel by loading of the indenter and outputting it as acoustic data.

8. The apparatus according to claim 7, further comprising a dynamic panel stiffness evaluator that evaluates dynamic panel stiffness of the outer panel based on the panel deformation data and the acoustic data.

9. The apparatus according to claim 5, wherein the apparatus comprises a sound collector collecting sound generated in deformation of the outer panel by loading of the indenter and outputting it as acoustic data.

10. The apparatus according to claim 9, further comprising a dynamic panel stiffness evaluator that evaluates dynamic panel stiffness of the outer panel based on the panel deformation data and the acoustic data.

* * * * *